United States Patent
Apostolos et al.

(10) Patent No.: US 9,030,202 B2
(45) Date of Patent: *May 12, 2015

(54) NQR DETECTION FROM CONTINUOUS RABI TRANSITIONS

(71) Applicants: John T. Apostolos, Lyndeborough, NH (US); Judy Feng, Nashua, NH (US); William Mouyos, Windham, NH (US); Benjamin McMahon, Nottingham, NH (US)

(72) Inventors: John T. Apostolos, Lyndeborough, NH (US); Judy Feng, Nashua, NH (US); William Mouyos, Windham, NH (US); Benjamin McMahon, Nottingham, NH (US)

(73) Assignee: AMI Research & Development, LLC, Windham, NH (US)

( * ) Notice: Subject to any disclaimer, the term of this patent is extended or adjusted under 35 U.S.C. 154(b) by 176 days.

This patent is subject to a terminal disclaimer.

(21) Appl. No.: 13/628,824

(22) Filed: Sep. 27, 2012

(65) Prior Publication Data

US 2014/0210464 A1   Jul. 31, 2014

Related U.S. Application Data

(60) Provisional application No. 61/540,851, filed on Sep. 29, 2011, provisional application No. 61/566,330, filed on Dec. 2, 2011.

(51) Int. Cl.
*G01V 3/00* (2006.01)
*G01R 33/36* (2006.01)
*G01N 24/08* (2006.01)
(Continued)

(52) U.S. Cl.
CPC .............. *G01R 33/36* (2013.01); *G01N 24/084* (2013.01); *G01R 33/441* (2013.01); *G01N 27/00* (2013.01); *G06F 17/18* (2013.01)

(58) Field of Classification Search
CPC ............................. G01R 33/441; G01R 33/446
USPC .......................................... 324/316, 322, 318
See application file for complete search history.

(56) References Cited

U.S. PATENT DOCUMENTS 5,457,385 A    10/1995   Sydney et al.
5,592,083 A *  1/1997   Magnuson et al. ........... 324/300
(Continued)

FOREIGN PATENT DOCUMENTS

JP    2009 264972 A    11/2009
WO   WO 2011/094462 A1   8/2011
(Continued)

OTHER PUBLICATIONS

Peshkovsky A. S. et al. "Noise-resilient multi-frequency surface sensor for nuclear quadrupole resonance," Journal of Magnetic Resonance, Academic Press, Orlando, FL, vol. 194, No. 2, Oct. 1, 2008, pp. 222-229.

(Continued)

*Primary Examiner* — Louis Arana
(74) *Attorney, Agent, or Firm* — Cesari and McKenna, LLP

(57) ABSTRACT

Nuclear quadrupole resonance measurement using two or more wire loop(s) within a space to define a portal, and driving the wire loop(s) with a baseband digital transmitter generating a chirped or stepped signal, to create a corresponding varying electromagnetic field within the portal. Coherent emissions reflected thereby are detected through a directional coupler feeding the transceiver. The detected coherent emissions are processed with a matched filter to determine presence of a target object within the portal.

25 Claims, 12 Drawing Sheets

(51) Int. Cl.
  *G01R 33/44* (2006.01)
  *G01N 27/00* (2006.01)
  *G06F 17/18* (2006.01)

(56) References Cited

U.S. PATENT DOCUMENTS

| | | | |
|---|---|---|---|
| 5,814,987 | A | 9/1998 | Smith et al. |
| 6,100,688 | A * | 8/2000 | Smith et al. ............ 324/300 |
| 6,127,824 | A * | 10/2000 | Smith et al. ............ 324/300 |
| 6,392,408 | B1 | 5/2002 | Barrall et al. |
| 7,868,758 | B2 | 1/2011 | Barral et al. |
| 7,999,541 | B2 | 8/2011 | Chisholm et al. |
| 8,660,803 | B2 * | 2/2014 | Apostolos et al. ............ 702/23 |
| 2006/0140249 | A1 | 6/2006 | Kohno |
| 2007/0018644 | A1 | 1/2007 | Flexman et al. |
| 2007/0096731 | A1 | 5/2007 | Peshkovsky et al. |

FOREIGN PATENT DOCUMENTS

| | | |
|---|---|---|
| WO | WO 2011/094463 A1 | 8/2011 |
| WO | WO 2011/094466 A1 | 8/2011 |
| WO | WO 2011/102948 A1 | 8/2011 |
| WO | WO 2011/126594 A2 | 10/2011 |
| WO | WO 2011/152887 A2 | 12/2011 |
| WO | 2013049270 | 4/2013 |

OTHER PUBLICATIONS

International Search Report and Written Opinion, mail date Dec. 20, 2012 for International Application No. PCT/US2012/057425, International Filing Date Sep. 27, 2012, AMI Research & Development, Inc. 15 pages.

Itozaki et al. "Nuclear Quadrupole Resonance for Explosive Detection" Graduate School of Engineering Science, Osaka, 560-8531, Japan, International Journal on Smart Sensing and Intelligent Systems, vol. 1, No. 3, Sep. 2008, pp. 705-715.

Apostolos, John T., et al., "Low-power stimulated emission nuclear quadrupole resonance detection system utilizing Rabi transitions," Proceedings of SPIE, SPIE—International Society for Optical Engineering, US, vol. 8709, Jun. 7, 2013, pp. 87090Q-1.

Hyde, J.S. et al., "W-band frequency-swept EPR" Journal of Magnetic Resonance, Academic Press, Orlando, FL,US, vol. 205, No. 1, Jul. 1, 2010, pp. 93-101.

Gupta, R. K. et al., "Rapid scan Fourier transform NMR spectroscopy," Journal of Magnetic Resonance, Academic Press, London, GB, vol. 13, No. 3, Mar. 1, 1974, pp. 275-290.

International Search Report and Written Opinion mail date Jul. 30, 2014 for International Patent Application No. PCT/US2014/025196 filed on Mar. 13, 2014 by AMI Research & Development, LLC, 15 pages.

* cited by examiner

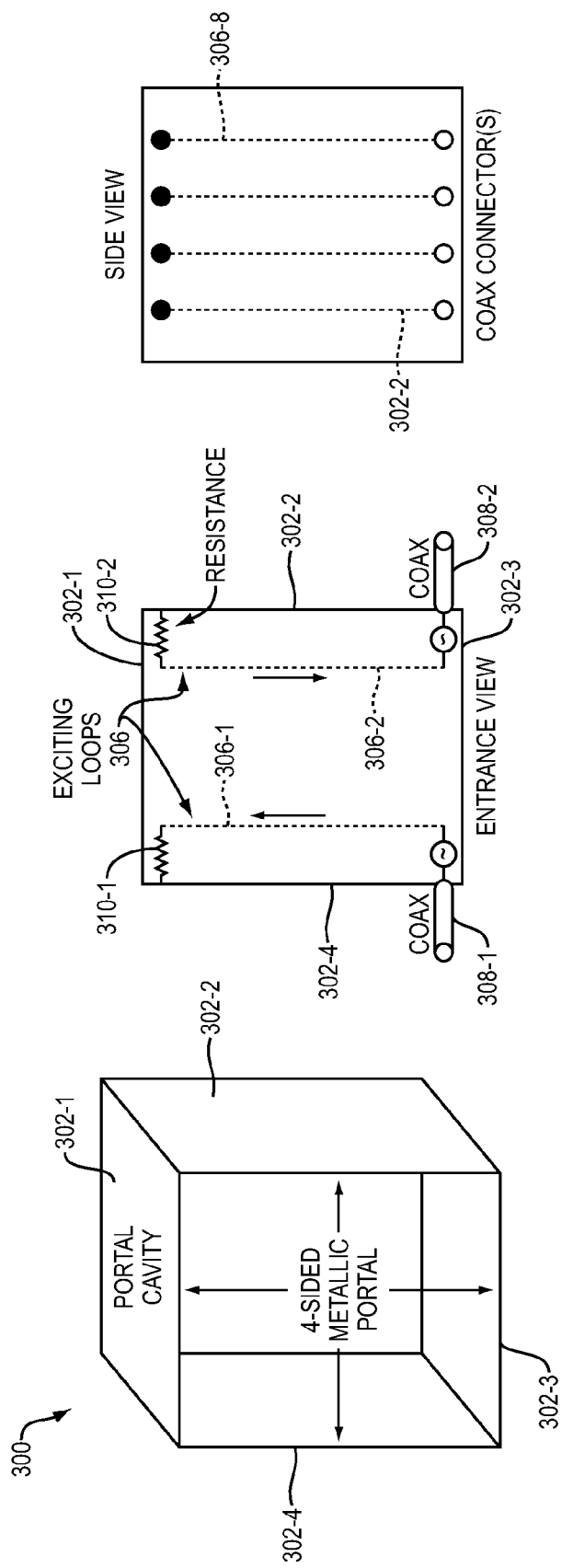

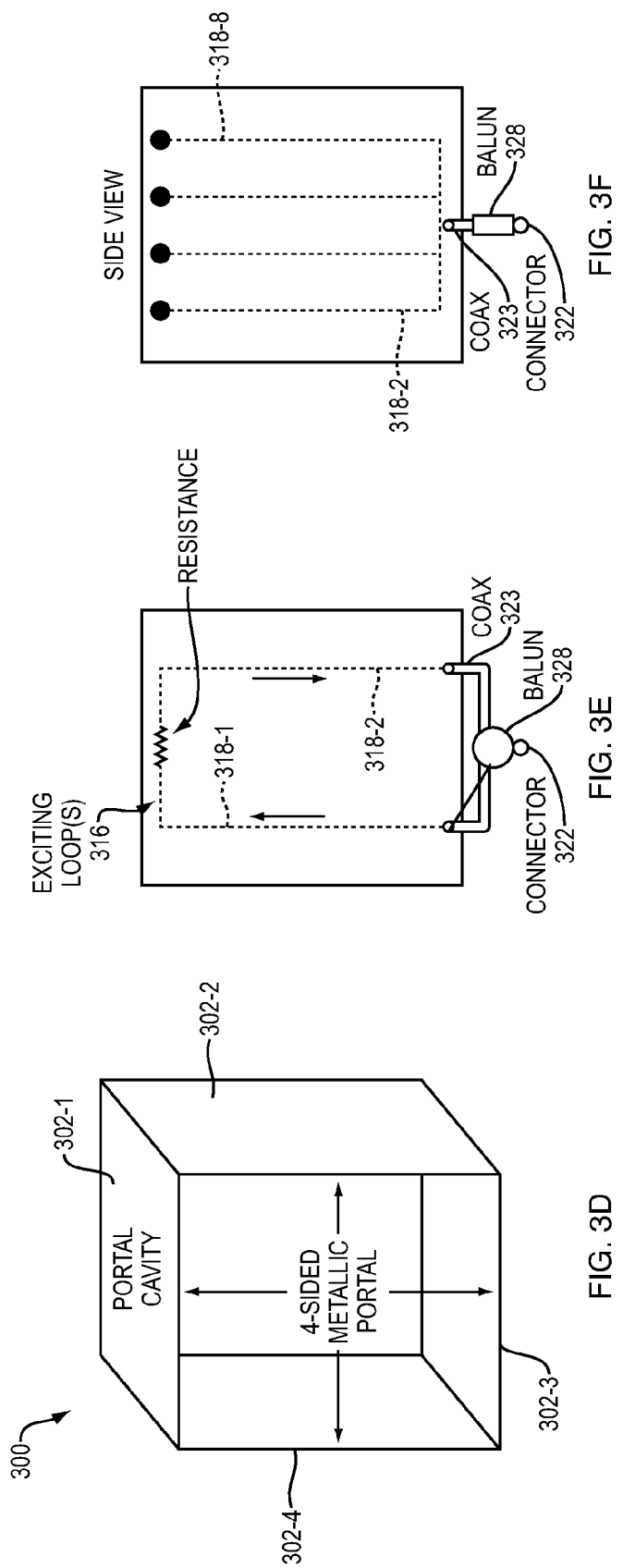

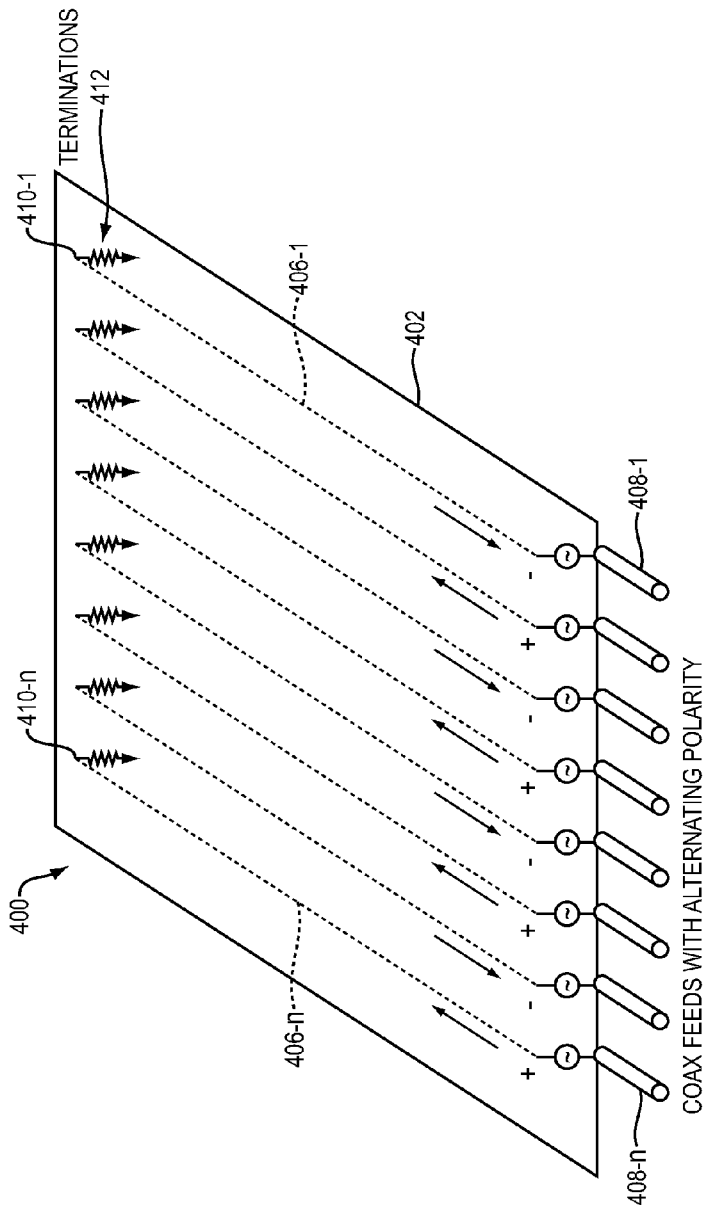
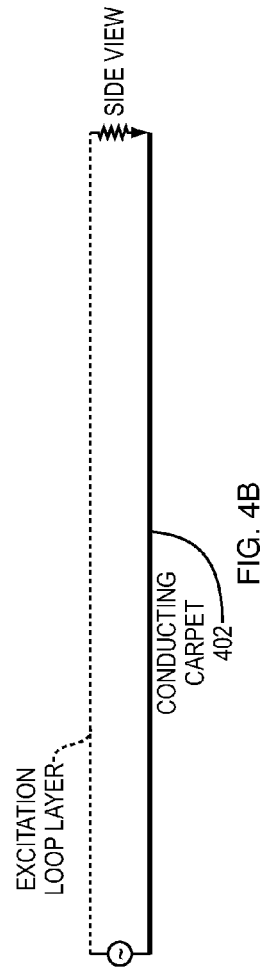
FIG. 4A
FIG. 4B

NQR DETECTION FROM CONTINUOUS RABI TRANSITIONS

RELATED APPLICATION

This application claims priority to U.S. Provisional Application No. 61/540,851, filed on Sep. 29, 2011 and U.S. Provisional Application No. 61/566,330 filed on Dec. 2, 2011. The entire teachings of the above application(s) are incorporated herein by reference.

BACKGROUND

This application relates to chemical analysis and more particularly to systems and methods that use nuclear magnetic resonance.

It is known that an atom with more than one unpaired nuclear particle (protons or neutrons) will have a charge distribution which results in an electric quadrupole moment. Allowed nuclear energy levels are shifted unequally due to the interaction of the nuclear charge with an electric field gradient supplied by the non-uniform distribution electron density (e.g. from bonding electrons) and/or surrounding ions. This so-called Nuclear Quadrupole Resonance (NQR) effect results when transitions are induced between these nuclear levels by an externally applied radio frequency (RF) field. This electromagnetic field thus induces a magnetic resonance, unique to each material, without using a magnet. A typically NQR detection system consists of a radio frequency (RF) power source, an emitter to produce the electromagnetic excitation field, and a detector circuit which monitors for a RF NQR response coming from the object being analyzed.

NQR has a number of practical uses, such as the detection of land mines, or of narcotics or explosives concealed in luggage, or remote monitoring of fluid levels such as in oil wells.

SUMMARY

In a first aspect, a technique for detecting a substance uses one or more conductive surfaces to define a space that is to be monitored. Two or more wire loops are disposed within the space typically adjacent the conductive surfaces. The wire loops are each individually electrically terminated in a preferred arrangement; alternatively, they can be arranged as balanced transmission lines. The wire loops are then driven with a radio frequency (RF) transmitter to create a time varying electromagnetic field within the defined space. The wire loops are, in one arrangement, individually electrically terminated through a respective resistance to a reference point, such as a ground voltage reference point.

The wire loops are connected to the transmitter via a directional coupler or in a similar fashion that avoids the use of ferrite material that might otherwise introduce nonlinearities in the system. The time varying electromagnetic field stimulates nuclear quadrupole resonance in any material with an electric quadrupole moment located within the space to cause the material to emit coherent RF emissions. These RF emissions are then detected using the same directional coupler through which the transmitter is connected. The received emissions are then further processed to determine characteristics of the substance, such as by detecting their amplitude, phase and/or frequency.

The NQR response for a given material is characterized as behaving according to the Rabi formulation that predicts a likelihood that the stimulated emission is either in the ground state or the excited state. We have realized that if the resonant frequency for a particular material of interest is known, the power incident on the material is known, and the exication signal is known (such as a chirp), the NQR response can be characterized. Thus the emissions can be continuously processed using a suitable matched filter to optimize detection.

It can also be discerned that a deterministic phase relationship exists between the reference and the emitted signal that depends on the circuitry used to generate the two. In other words, the phase difference between the reference and the signal to be detected should account for path differences in the circuits used to generate the two different signals. A criterion can then be set up to accept or reject a potential authentic NQR response signal based upon how close the measured tracked phase matches the theoretical expected phase.

In one particular arrangement the conductive surfaces are configured as a generally rectangular portal of convenient size, such as large enough to permit a person to walk through. In this arrangement, one or more wire loops are disposed adjacent a first vertical conductive surface and one or more wireless are also disposed along a second opposite vertical conductive surface. If multiple wires are disposed adjacent a given surface they can be driven with alternating polarities of RF signals.

In another arrangement, a single conductive surface can be disposed such as in a floor or ceiling to define the space. In this example, it would be typical for many wire loops to be disposed in the floor or ceiling adjacent the conductive surface but remaining within the space, again with alternating polarities.

The emitted RF signal will optionally take the form of a frequency stepped or chirped signal centered about a specific radio frequency that is known to be related to the NQR of a substance of interest. If a system is to detect multiple substances of interest therefore, it will be advantageous to emit multiple such signals centered around different carrier frequencies that correspond to resonances of the materials of interest. Thus corresponding detector will also detect coherent emissions such as with the corresponding number of RF filters.

In still other arrangements, a single RF transmitter and receiver can be used to operate multiple portals. In this arrangement, the different portals each have their respective sets of wire loops. These wire loops in the different portals are driven with orthogonal modulated RF signals, such as by using Code Division Multiple Access (CDMA). The corresponding orthogonal demodulation process is implemented on the receiving end.

Detection performance can be improved by determining a reference emission when the portal is empty. This empty portal response is compared to signal(s) detected when a substance is placed in the portal. However the comparison is not direct; in a preferred arrangement, complex-valued reference signal points are averaged to determine a start point and a stop point of a reference line that extends from a beginning sweep amplitude and frequency to an ending sweep amplitude and frequency. The signal points of a detected emission from an object are then similarly average to determine a start point and stop point. A difference is then determined that is taken as a difference between the signal and these reference lines as the detected emission.

BRIEF DESCRIPTION OF THE DRAWINGS

The description below refers to the accompanying drawings, of which:

FIGS. 3A, 3B and 3C illustrate a loop-excited space defining a cavity portal; the excitation is with individual resistor terminations.

FIGS. 3D, 3E and 3F illustrate another excited portal arrangement using balanced transmission lines excitation.

FIGS. 4A and 4B show a conducting half space layer placed on a floor.

DETAILED DESCRIPTION OF AN EMBODIMENT

Historically, systems that make use of the Nuclear Quadrupole Resonance (NQR) effect to detect substances have used a large pulsed radio frequency (RF) magnetic field followed by detection of a weak RF field. These fields are typically in the 1 MegaHertz (MHz) range. As a result, most prior existing NQR systems require high power, are large and bulky, and suffer from low sensitivity. The enhanced NQR detection system described will have one or more distinguishing characteristics.

Rabi Formulation to Characterize Continuous System Response

A formulation known as the Rabi formulation characterizes the response of an atom to an applied harmonic field, when the applied frequency is close to the atom's natural frequency. A simple approach is through a two-energy level approximation, in which one only treats two energy levels of the atom in question. No atom with only two energy levels exists in reality, but a transition between, for example, two hyperfine states in an atom can be treated, to first approximation, as if only those two levels existed, assuming the drive is not too far off resonance.

Thus the NQR of a substance can be characterized using the general Rabi formulation in which the nucleus is assumed to oscillate between state 1 (a ground state) and state 2 (an excited state) under the influence of the time-dependent incident electromagnetic field. This implies that the nucleus alternatively absorbs energy from the incident field and emits coherent energy induced by the incident field. The phenomenology is expressed by Rabi's equations below (Equations 1 and 2).

$$P_1(t) = 1 - P_2(t) \tag{1}$$

$$P_2(t) = \frac{\gamma^2}{\gamma^2 + (\omega - \omega_{NQR})^2/4} SIN^2(\Omega t) \tag{2}$$

$$\Omega = [\gamma^2 + (\omega - \omega_{NQR})^2/4]^{1/2}$$

where P1 is the probability that the nucleus is in the ground state and P2 is the probability that the nucleus is in the excited state. $4\gamma$ is the half power width. The SIN term in Equation 2 expresses the periodic nature of the emissions.

Using these Rabi formulations (Equations 1 and 2), if the NQR resonant frequency, $\omega_{NQR}$, and variations in the power incident on a material are known, a matched filter can be determined to optimized signal detection.

For the case of detecting Sodium Nitrite, a material with known NQR frequencies, the NQR signal response can be predicted assuming, for example, that the incident field is a chirp waveform. The chirp instantaneous frequency is given by Equation 3:

$$\omega_{INSTANTANEOUS} = F_{START} 2\pi + 2\pi (BW/T)t \tag{3}$$

For the known Sodium Nitrite NQR frequency at 3607 kHz, the following values are applicable:

BW=40 kHz
T=1 sec
$4\gamma$=100 Hz

The signal response 100 is estimated by convolving the chirp waveform with the inverse Fourier transform of Equation 2.

Figure 1:
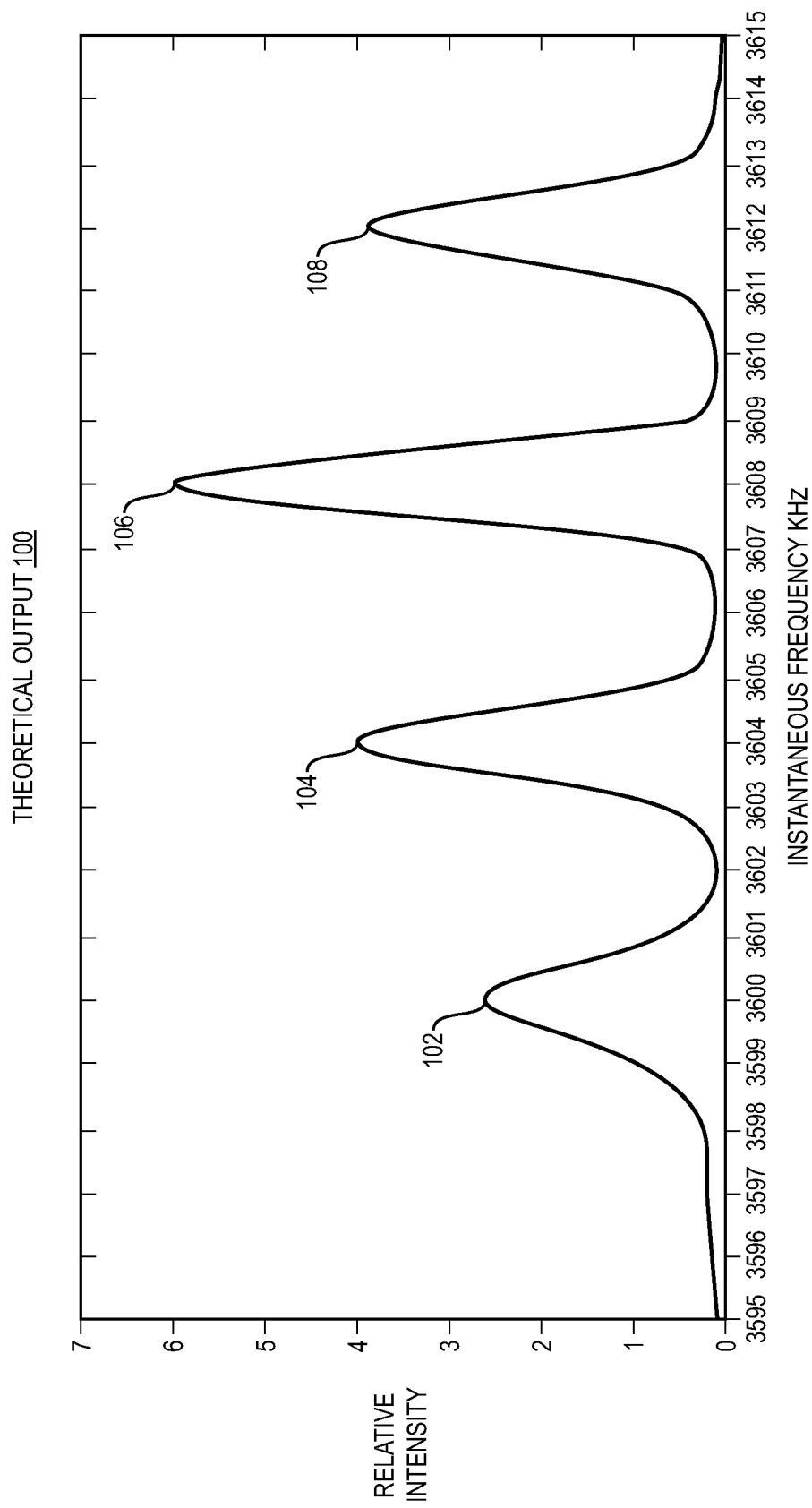
FIG. 1 is a theoretical plot of continuous NQR coherent emissions from sodium nitrate that result from a chirp excitation signal.
Figure 2:
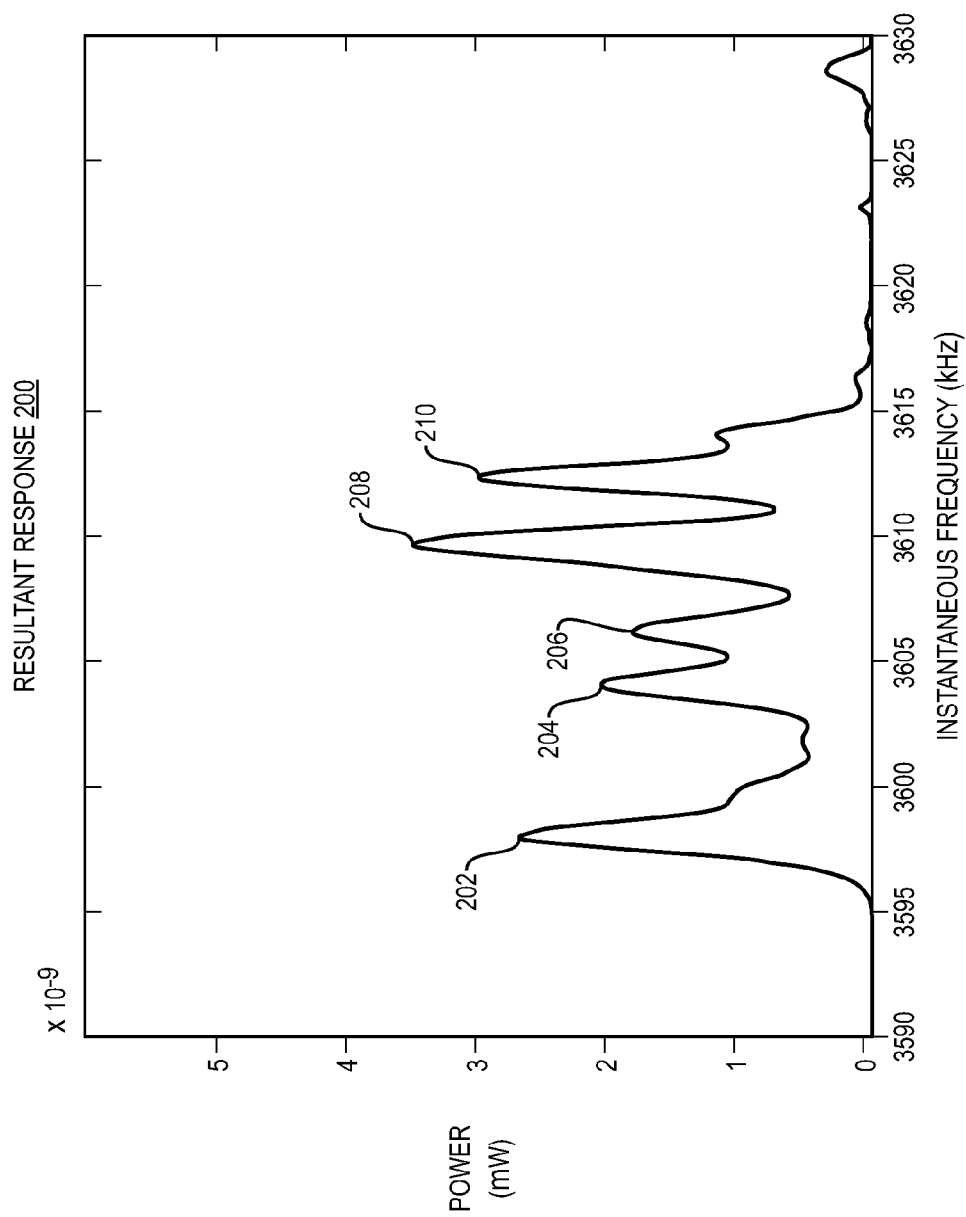
FIG. 2 is an actual measured response for sodium nitrate.

FIG. 1 shows simulation results of the sodium nitrite NQR resonance using Equation 2. The pulsed RF represents the periodic coherent emissions centered at 3607 KHz. Note the estimated four energy peaks, 102, 104, 106 and 108. FIG. 2 illustrates actual measured data from a sodium nitrate sample. Note the energy peaks 202, 204, 206, 208, 210 correspond more or less, but not exactly, to the theoretical model. This difference is typically acceptable, as the system can store templates of actual response measurements for different materials.

A matched filter is then used to coherently integrate all the pulsed emissions as part of the detection process.

Conductive Surfaces Define a Space

In a practical implementation, one or more conductive surfaces are arranged to define a space that is to be monitored such as for access control. FIGS. 3A, 3B and 3C illustrate one such cavity type arrangement where a generally rectangular portal 300 is defined by four conductive walls 302-1, 302-2, 302-3, 302-4. Two or more wire loops 306-1, 306-2 are disposed within the space, typically adjacent selected ones of the conductive surfaces 302. The wire loops 306 are each individually electrically terminated through a resistance 310 to the respective conductive wall(s) in this arrangement. A coaxial cable connector 308-1, 308-2 provides connection to the radio frequency (RF) transmitter and receiver. The conductive walls 302 define the space within which a uniform electromagnetic field can be maintained by the wire loop radiators while at the same time protecting the space from outside disturbances.

FIGS. 3D, 3E and 3F show another possible arrangement of the wire loops. There, the wire loops 316 are still disposed within the cavity 300. However, they are implemented as a balanced transmission line driving two segments 318-1, 318-2 through a balun 328 with the two segments 318-1, 318-2 having a resistance 320 disposed at their mid-point.

In another arrangement, the space to be monitored is defined as a conductive half-space 410. A system of wire loops 410 provides excitation to such a conductive half space 400, such defined by a metal surface 402 embedded in a floor, as shown in FIGS. 4A and 4B. The half space 400 can be a corridor or large open public area. In the illustration of FIGS. 4A and 4B, the loops 410 are individually fed by coax feeds 408, and terminated by resistors 412. The coax feeds 408 may have alternating polarities, as shown. The excitation loop(s) layer and the conducting half space layer can comprise a composite flexible carpet, in one example.

System Hardware Components

Figure 5:
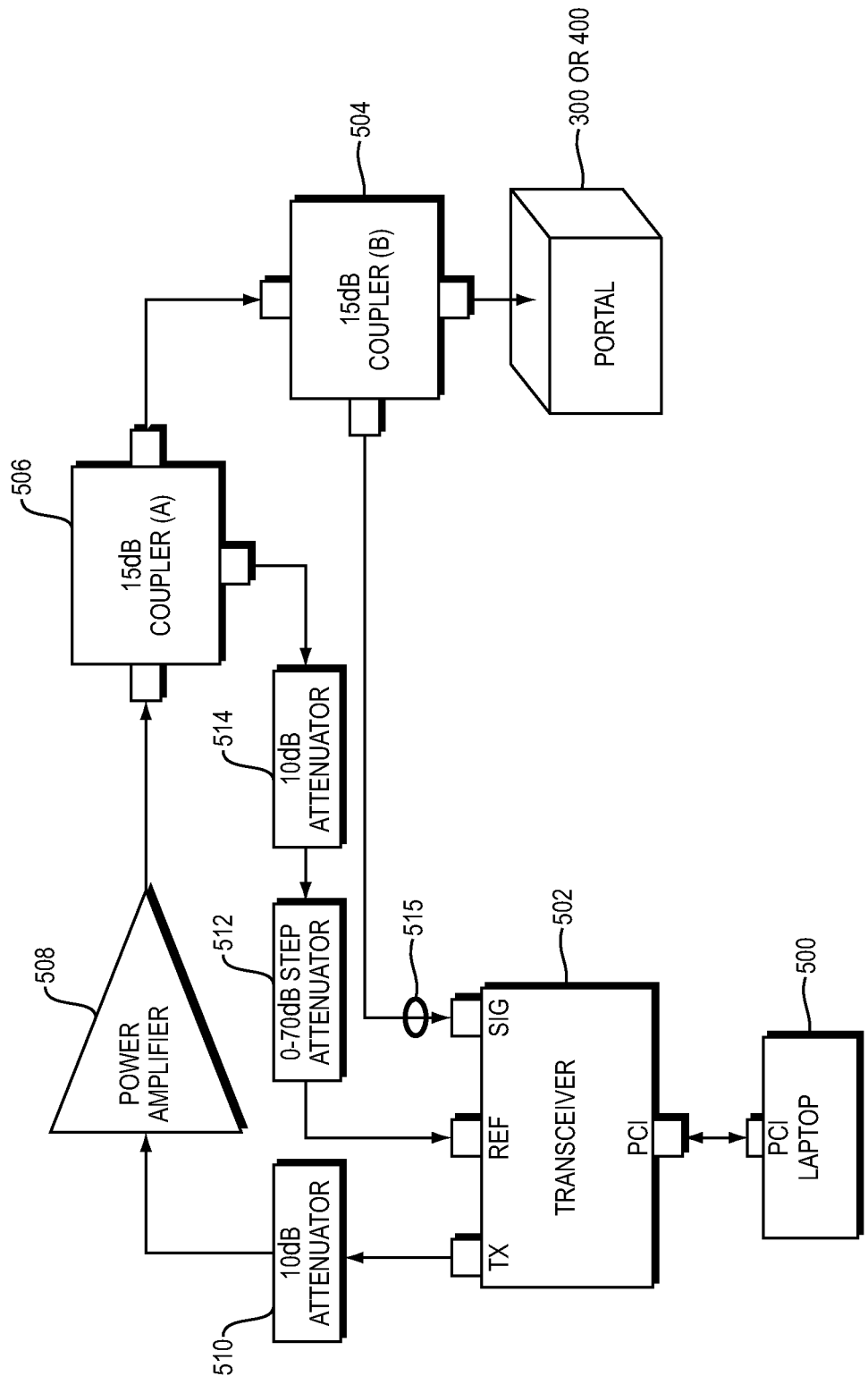
FIG. 5 is a general block diagram of the system.

The preferred embodiment of the NQR electronics is shown in FIG. 5 for a single portal, single frequency band. A laptop computer 500 or other data processor or digital signal processor controls a transceiver 502. The transceiver 502 generates a transmit waveform, Tx, and receives receive signal Sig and reference signal Ref. The transmit signal Tx is fed through a power amplifer 508 and attenuator 510 to a first directional coupler A 506. A first output of directional coupler A 506 is fed to a second directional coupler B 504. The directional coupler B 504 then feeds the wire loops in the portal 300 or 200 to to create a time varying electromagnetic field within the space. The use of directional couplers 504, 506 that do not incorporate any ferrite material is preferred, to avoid introducing nonlinearities in the system.

A baseband digital source 502 generates the chirp or stepped waveform under control of the computer 500. This waveform is amplified and excites the portal 300 or 400, creating a field which envelopes a person walking through. If explosives are being carried by the person, the coherent emissions are reflected through directional coupler (B) 504 at the portal 300, 400 and fed to the transceiver signal input (515). The functionality of each component of the block diagram of FIG. 5 is therefore as follows:

Laptop Computer (500): Executes a detection algorithm, such as by using a stored computer program, processes raw data from the transceiver, and outputs the NQR response. Could also be a digital signal processor or other suitable machine.

Transceiver (502): Generates the input waveform and handles the reference and coherent emission returns.

Power Amplifier (508): Amplifies the signal in order to excite the portal.

15 dB Directional Coupler (A) (506): Provides a reference for the system which is fed back into the transceiver.

15 dB Directional Coupler (B) (504): Feeds coherent emissions reflected from the portal back into the transceiver.

Portal (300 or 400): Field detector.

Attenuators (510, 512, 514): Control power levels necessary for the power amp 508 and transceiver 502.

In operation a "baseline" signal using an empty portal is continuously recorded by the computer 500. As described in more detail below, the baseline signal is then differentially combined with the signal acquired from the person or other object in the portal.

System Software Components

Waveform Genreation

The material detection system requires an input waveform which is created and/or stored by the computer 500 and fed into the transceiver 502 to generate the transmit waveform Tx. The transmit waveforms of interest are 1) a Chirp Waveform and 2) a Stepped Frequency Waveform, Equations 4 and 5 respectively.

The chirp waveform is generated according to:

$$\sin(F_{start} 2\pi t_l + \pi(\Delta/T)t_l^2) \qquad (4)$$

$\Delta = F_{stop} - F_{start}$
$\Delta = 40$ kHz
T=(Dwell Interval)×400=1 sec
Dwell Interval=$2.5 \times 10^{-3}$ sec
$t_l$=l/sample rate $1 \leq l \leq$(sample rate×T)

The stepped frequency waveform can be given by:

$$\sin(F_N 2\pi t_l) \qquad (5)$$

401 Frequencies within a 40 kHz Band
400 intervals, $(40 \times 10^3/400)$=100 Hz steps
Every Dwell Interval=$2.5 \times 10^{-3}$ sec
Step $F_N \rightarrow F_{N+1}$
$F_1 = F_{start}$, $F_{401} = F_{stop}$
$\Delta = F_{stop} - F_{start}$
$\Delta = 40$ kHz
T=(Dwell Interval)×400=1 sec
Dwell Interval=$2.5 \times 10^{-3}$ sec
$t_l$=l/sample rate $1 \leq l \leq$(sample rate×T)

The use of ferrite-free directional couplers permits the detection of stimulated emissons that are as small as $10^{-8}$ to $10^{-10}$ of the transmit power incident on the material.

Detection Processing

Figure 6:
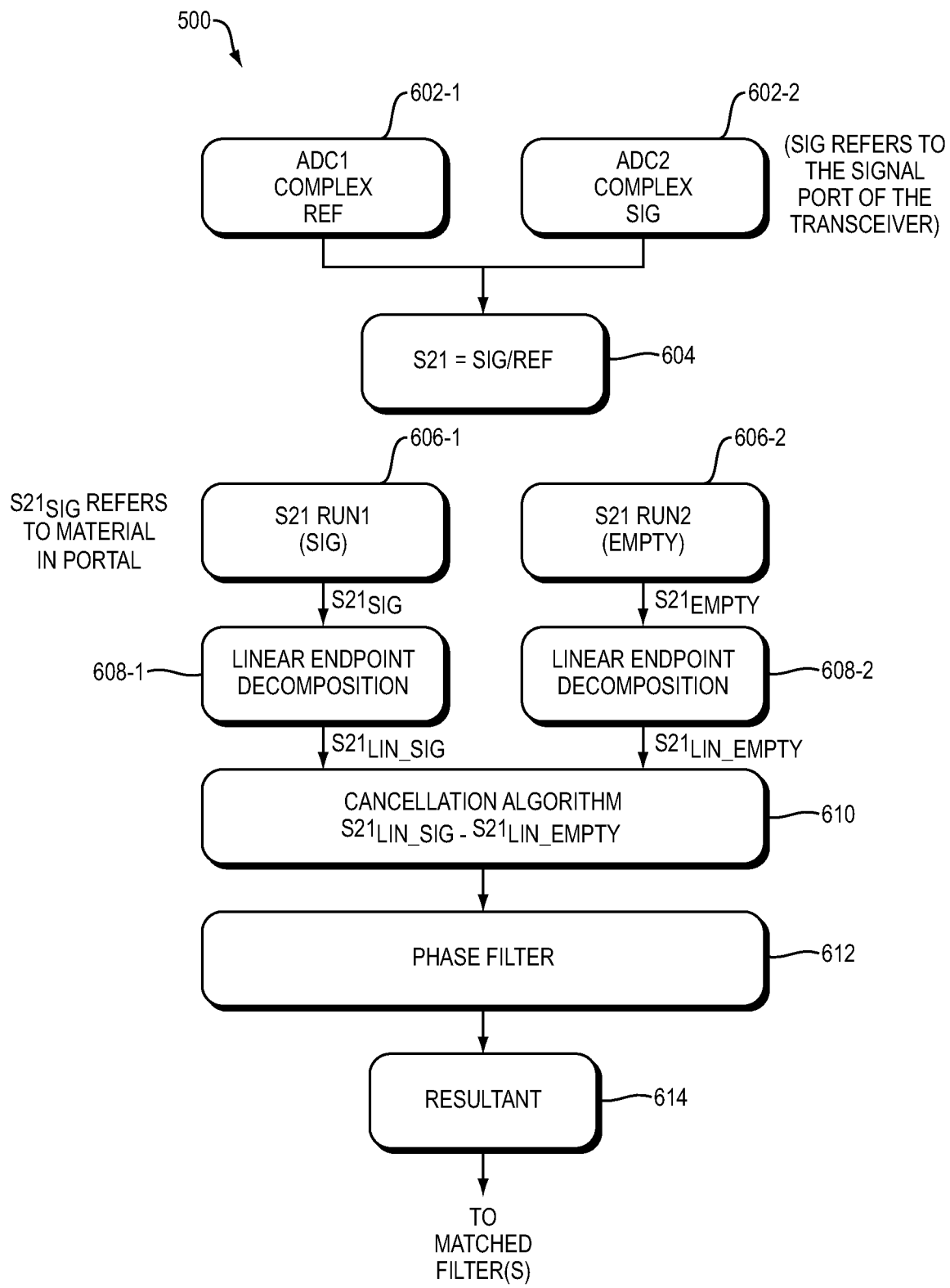
FIG. 6 is a more detailed view of processing the detected emissions.

FIG. 6 is a flow diagram of the receive processing implemented or controlled by the computer 500. It should be understood that these functions can be carried out entirely in software, or in special purpose digital signal processing hardware, or a combination of both. The general idea is to take a set of measurements with an empty portal 300, 400, and process those along with a set of prior measurements taken with the material of interest in the portal 300, 400.

Responses from the portal are processed as follows.

In a first step 602-1, a complex-valued (I and Q) reference signal is obtained at the Ref input of the transmiter 502 and converted to digital data through an Analog to Digital converter (ADC). The signal port (Sig) provides a complex-valued signal at the same time. S21 (Sig/Ref) is then determined in step 604.

Two data runs are then performed—one with material of interest located in the portal (step 606-1) and one run with the empty portal (step 606-2).

A corresponding linear end point decomposition (steps 608-1 and 608-2) is then performed on each measurement. This decomposition is described in more detail in connection with FIG. 7 below.

Next, a cancellation algorithm is applied in step 610 to remove the effect of the portal on the measurement.

Finally, a phase filtering operation (step 614) is applied to remove artifacts of phase differences in the reference and signal paths, to obtain the response that is considered the response due only to NQR of the material.

Figure 7:
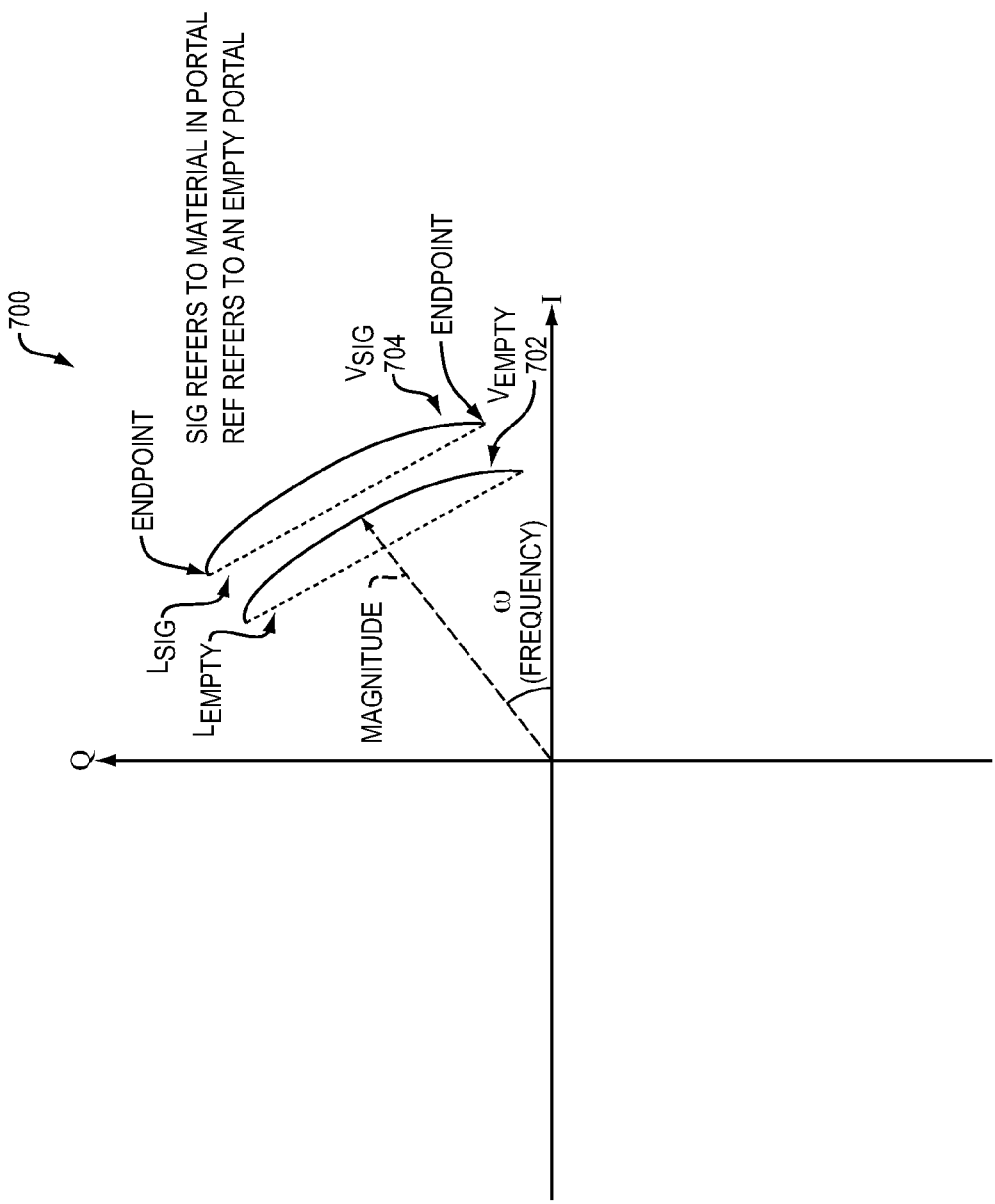
FIG. 7 is a pictorial representation of one aspect of the processing.

More particularly, steps 608-1 and 608-2 normalize raw data received from the portal, $V_{SIG}$, with material in it, it using reference data received from an empty portal, $V_{EMPTY}$, previously collected. $V_{SIG}$, data received from the portal with material in it, and $V_{EMPTY}$, data from the portal without material in it, are complex functions. FIG. 7 shows such an example $V_{SIG}$ and $V_{EMPTY}$ plotted on the I and Q complex-valued plane. Each data point is represented as a vector magnitude and frequency (angle). The responses $V_{EMPTY}$ and $V_{SIG}$ thus manifest as a moving vector in the complex plane.

Average segments, $L_{SIG}$ and $L_{EMPTY}$, are then developed and then compared to the measured values. More particularly, respective start and stop points of $L_{SIG}$ and $L_{EMPTY}$ are obtained by averaging $V_{SIG}$ and $V_{EMPTY}$ over a small percentage of the input sweep signal centered at the endpoints of each respective segment. $L_{SIG}$ and $L_{EMPTY}$ are straight line segments.

$$V_{OUT} = (V_{SIG} - L_{SIG}) - (V_{EMPTY} - L_{EMPTY}) \qquad (6)$$

The intermediate output, $V_{OUT}$ (Equation 6) is then applied to a phase matching step and then the coherent pulse train matched filter for the final NQR output, (example coherent pulse trains were shown in FIGS. 1 and 2.)

Phase Matching

Since the NQR signal of interest is derived from the stimulated emission of the excited states of the nucleus, there is also a deterministic phase relationship between the reference and the NQR signal of interest.

Figure 8:
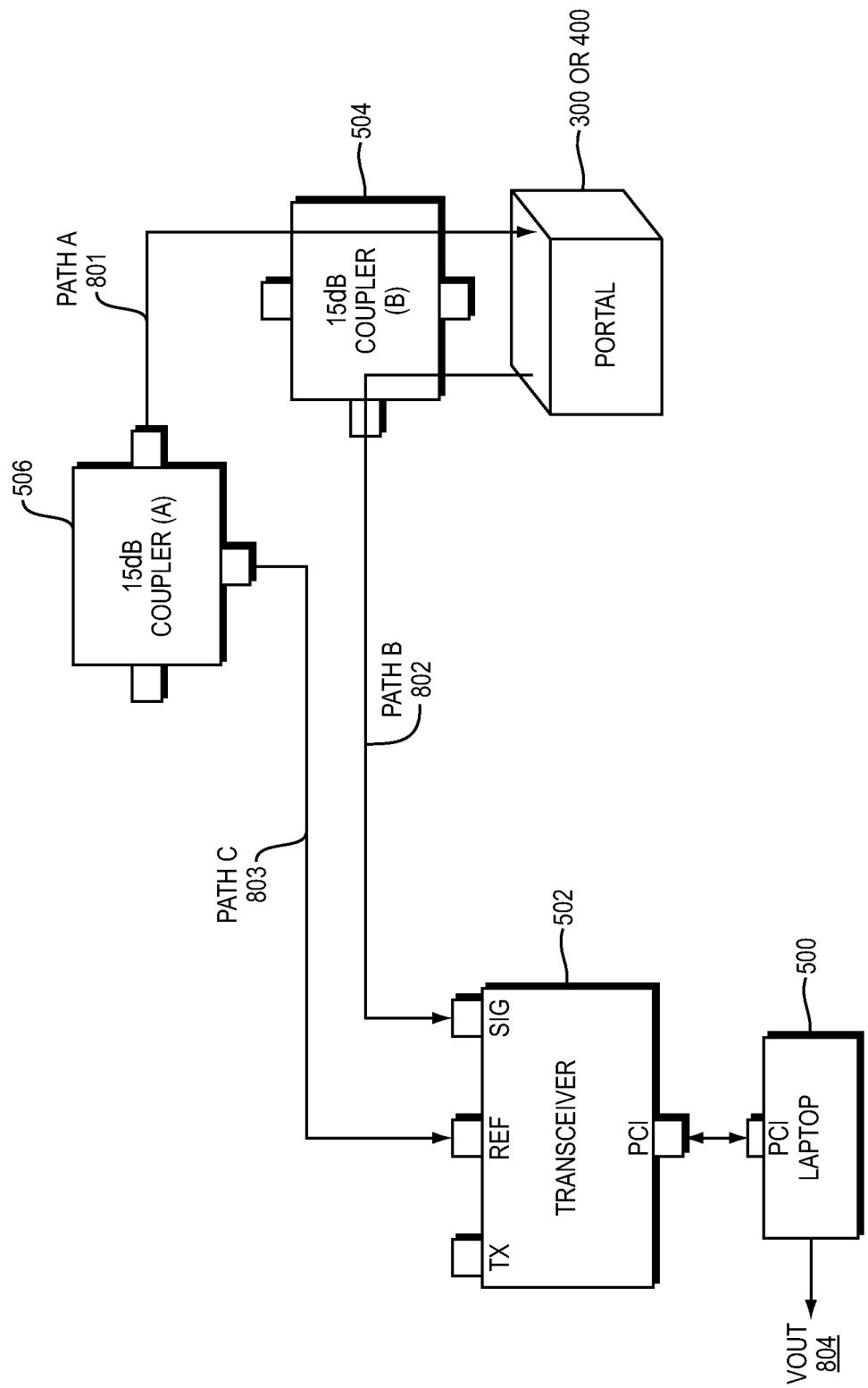
FIG. 8 is a general block diagram showing signal paths.

The phase difference between the reference and the NQR signal can thus be determined by considering the path differences of the reference (path C) and the signal (path B+path A) through the system. These differences depend upon the delay in paths A, B, and, C as depicted in FIG. 8.

The end result of the above relationships is that $V_{OUT}$ (Equation 6), which is calculated from reference and signal measurements, represents the actual stimulated emission output (NQR signal) and has a deterministic phase (all phases are measured relative to the reference channel).

A criterion can be set to accept or reject a potential authentic NQR signal, based on how close the measured phase tracks the theoretical phase. A library of expected responses from a set of materials is the developed from actual measurements. The library may include responses under different conditions known to affect NQR such as temperature, humidity, etc.

Decision/Matched Filtering

As alluded to above, a final step is to match the resultant response against one or more known response(s) to determine the type of material detected. This matching process can match against a library of templates of previously detected responses (such as FIG. 2) or theoretical expected responses (such as FIG. 1). The matching may compare amplitude peaks and corresponding phases, or may be a more mathematically robust matched filter.

Single Portal, Multiple Frequency Bands Implementation

In order to handle multiple frequency bands simultaneously for a single portal configuration, Frequency-Division Multiple Access (FDMA) is employed. With this approach, multiple transmit signals, siuch as multiple chirp signals, are generated at different RF carriers. The receiver can then use a corresponding set of frequency domain frequency filters which are accessed within the transceiver.

Figure 9:
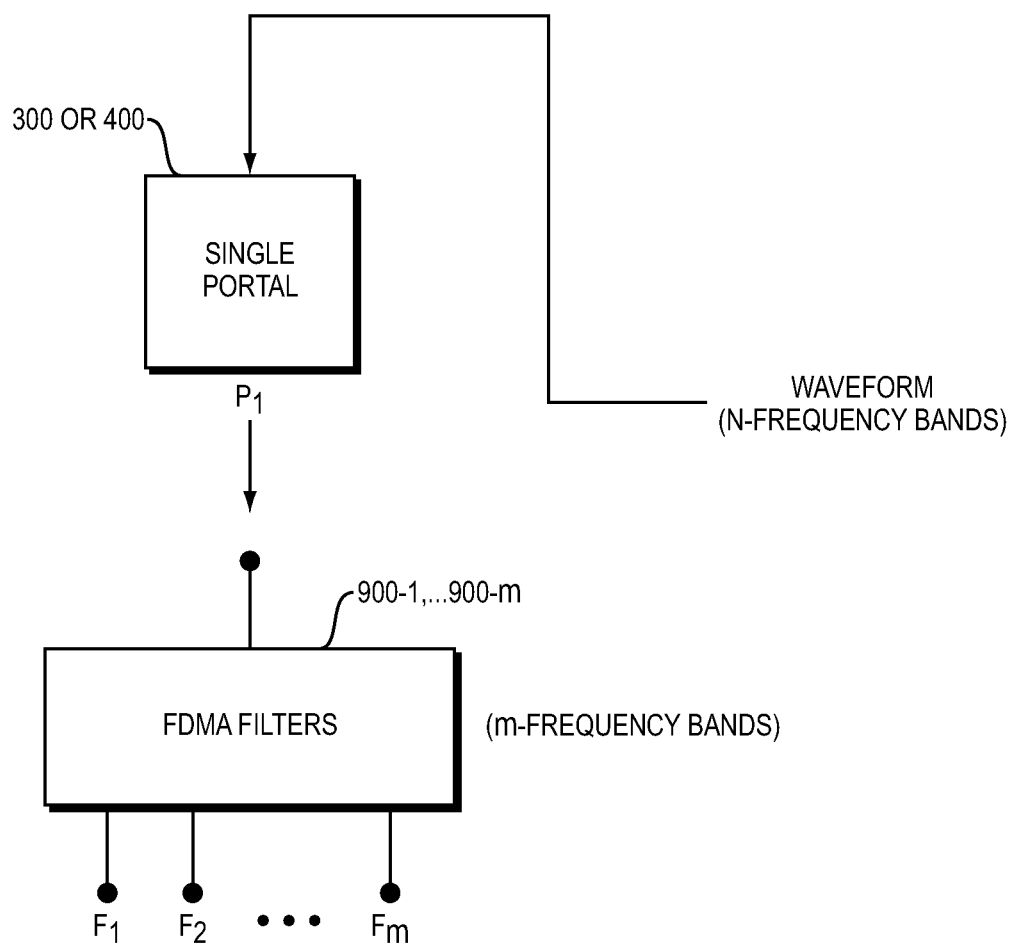
FIG. 9 is a single portal multiple frequency block diagram.

The block diagram of this single portal, multiple frequency bands implementation is shown in FIG. 9.

Multiple Portals, Multiple Frequency Bands Implementation

Figure 10:
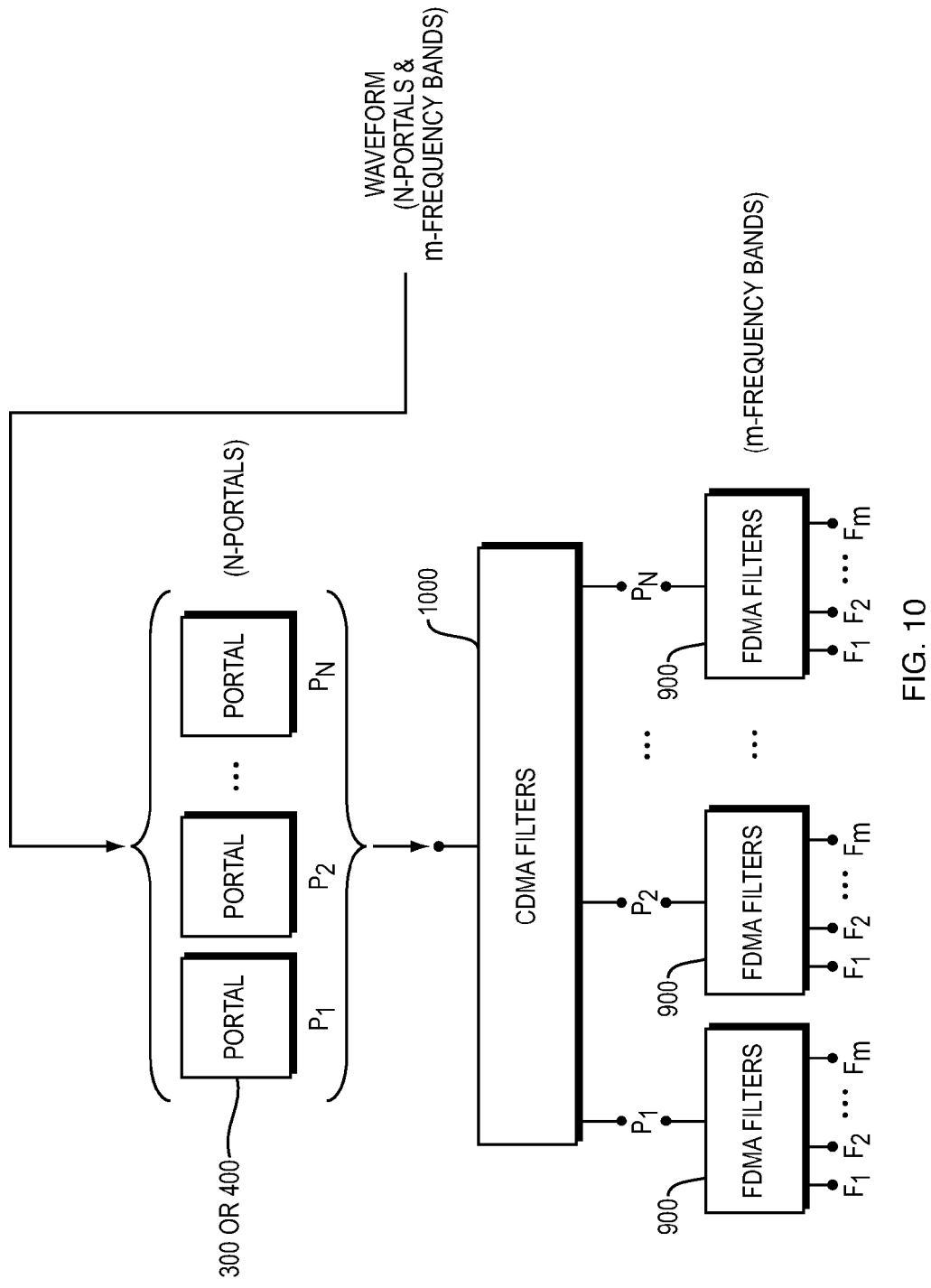
FIG. 10 illustrates a multiple-portal, multiple frequency system.

It is also possible to run a multiple portal, multiple frequency band system with some modifications to the single portal, single frequency band system architecture. The general block diagram for a multiple portal, multiple frequency band system is shown in FIG. 10; the modification is to use Code Division Multiple Access (CDMA) or some other orthogonal modulation scheme to separate the signals associated with different portals.

Thus, in order to simultaneously handle multiple portals and multiple frequency bands, Code-Division Multiple Access (CDMA) and Frequency-Division Multiple Access (FDMA) are both employed. CDMA handles multiple portals simultaneously and then filters the information from each of the multiple portals through de-coding. These de-coded responses are then fed through FDMA filters which frequency divides the simultaneous frequency band information from each portal.

Figure 11:
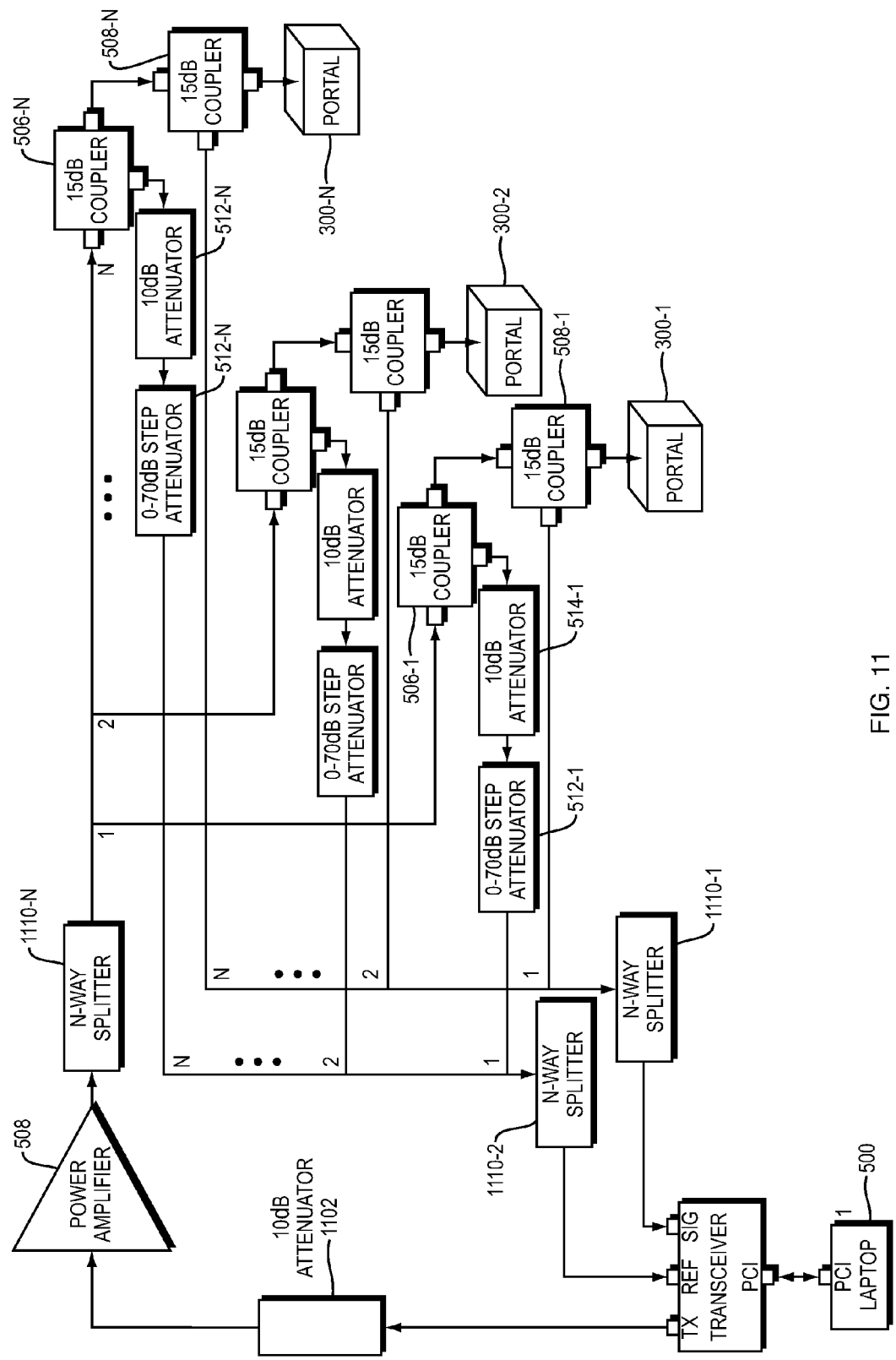
FIG. 11 is a more detailed view of the multiple portal, multiple frequency band system.

Ultimately, the sophisticated waveform input (N-Portals, m-Frequency Bands) that is fed into the material detection system is able to handle N-Portals and m-Frequency Bands simultaneously while giving filtered output that is portal and frequency band binned so that the separate responses are of value. A high level block diagram of the multiple portals, multiple frequency bands implementation is shown in FIG. 10, and in more detail in FIG. 11.

While this invention has been particularly shown and described with references to example embodiments thereof, it will be understood by those skilled in the art that various changes in form and details may be made therein without departing from the scope of the invention encompassed by the appended claims.

What is claimed is:

1. A method for detecting a substance comprising:
   disposing at least one conductive surface to define a space adjacent the conductive surface;
   disposing two or more wire conductors within the space adjacent the conductive surface;
   driving the wire conductors with a baseband chirped radio frequency transmitter through a directional coupler to create a time varying electromagnetic field within the space adjacent the conductive surface, the time varying electromagnetic field stimulating continuous transitions between two power states in the nucleus of the substance;
   receiving resulting coherent radio frequency emissions from the substance through the same directional coupler through which the transmitter is coupled; and
   processing the coherent radio frequency emissions with a radio frequency filtering step to determine characteristics of the substance.

2. The method of claim 1 wherein four conductive surfaces are disposed to define the space as a generally rectangular portal.

3. The method of claim 2 wherein a first wire conductor disposed within the space adjacent a first conductive surface, and a second wire conductor is disposed within the space adjacent a second conductive surface, with the second conductive surface located opposite the first conductive surface.

4. The method of claim 1 wherein the wire conductors are each individually electrically terminated through a respective resistance to a ground reference point.

5. The method of claim 2 wherein multiple wire conductors are disposed adjacent one another and adjacent a selected conductive surface, with adjacent wire conductors driven with radio frequency signals of alternating polarities.

6. The method of claim 1 additionally comprising:
   detecting a portion of transmitter power with a directional coupler, to provide a reference signal, and where the step of processing the coherent emissions further uses the reference signal to determine characteristics of the substance.

7. The method of claim 1 wherein the stimulated emissions are limited to between about $10^{-8}$ and $10^{-13}$ of the transmitted energy incident on the space.

8. The method of claim 1 wherein the conductive surface is disposed on one side of the space to define a conductive half-space.

9. The method of claim 1 wherein the directional coupler has a linear response.

10. The method of claim 1 wherein the directional coupler is free of ferrite material that would otherwise introduce non-linearities.

11. An apparatus for detecting a substance comprising:
   at least one conductive surface defining a space adjacent the conductive surface;
   two or more wire conductors located within the space adjacent the conductive surface;
   a directional coupler;
   a chirped or stepped radio frequency transmitter coupled to the wire conductors through the directional coupler to create a time varying electromagnetic field within the space, the time varying electromagnetic field stimulating continuous transitions between two states in the nucleus of the substance;
   a radio frequency receiver for receiving resulting coherent radio frequency emissions from the substance through the directional coupler; and a signal processor, for processing the coherent radio frequency emissions to determine characteristics of the substance.

12. The apparatus of claim 11 wherein four conductive surfaces are disposed to define the space as a generally rectangular portal.

13. The apparatus of claim 12 wherein a first wire conductor is disposed within the space adjacent a first conductive surface, and a second wire conductor is disposed within the space adjacent a second conductive surface, with the second conductive surface located opposite the first conductive surface.

14. The apparatus of claim 11 wherein the wire conductors are each individually electrically terminated through a respective resistance to a ground reference point.

15. The apparatus of claim 12 wherein multiple wire conductors are disposed adjacent one another and a selected conductive surface, with adjacent wire conductors driven with radio frequency signals of alternating polarities.

16. The apparatus of claim 11 additionally comprising:
a second directional coupler, arranged to detect a portion of transmitter power as a reference signal.

17. The apparatus of claim 11 wherein the stimulated emissions are limited to between about $10^{-8}$ and $10^{-13}$ of the transmitted power energy incident on the space.

18. The apparatus of claim 11 wherein the conductive surface is disposed on one side of the space to define a conductive half-space.

19. The apparatus of claim 11 wherein the directional coupler has a linear response.

20. The apparatus of claim 1 wherein the directional coupler is free of ferrite material that would otherwise introduce non-linearities.

21. An apparatus for detecting a substance comprising:
at least four conductive surfaces spaced apart from one another to define a rectangular cavity;
two or more wire conductors located within the cavity, each of the two or more wire loops disposed adjacent one of the conductive surfaces;
a chirped radio frequency transmitter coupled to the wire conductors, to create a time varying electromagnetic field within the cavity, the time varying electromagnetic field stimulating continuous transitions between two energy states in the nucleus of a substance disposed within the cavity; and
a radio frequency receiver for receiving resulting coherent radio frequency emissions from the substance.

22. The apparatus of claim 21 wherein a first wire conductor is disposed within the cavity space adjacent a first conductive surface, a second conductor is disposed within the cavity adjacent a second conductive surface, with the second conductive surface located opposite the first conductive surface.

23. The apparatus of claim 21 wherein the wire conductors are each individually electrically terminated through a respective resistance to a ground reference point on a respective one of the conductive surfaces.

24. The apparatus of claim 21 wherein multiple wire conductors are disposed adjacent one another and adjacent a same selected one of the conductive surfaces, with adjacent ones of the wire conductors driven with radio frequency signals of alternating polarities.

25. The apparatus of claim 21 wherein the wire conductors are each electrically terminated to provide a uniform electromagnetic field within the cavity.

* * * * *

UNITED STATES PATENT AND TRADEMARK OFFICE
CERTIFICATE OF CORRECTION

| | | |
|---|---|---|
| PATENT NO. | : 9,030,202 B2 | Page 1 of 1 |
| APPLICATION NO. | : 13/628824 | |
| DATED | : May 12, 2015 | |
| INVENTOR(S) | : John T. Apostolos et al. | |

It is certified that error appears in the above-identified patent and that said Letters Patent is hereby corrected as shown below:

In the Claims:
Claim 3, Col. 8, line 25 should read:
is disposed within the space adjacent a first conductive surface Claim 22, Col. 10, line 17 should read:
ductive surface, a second wire conductor is disposed within the Signed and Sealed this
Twenty-fifth Day of August, 2015

Michelle K. Lee
*Director of the United States Patent and Trademark Office*